United States Patent
Hofmann et al.

(10) Patent No.: US 6,614,228 B2
(45) Date of Patent: Sep. 2, 2003

(54) DEVICE FOR TRAPPING AT LEAST ONE COMPONENT OF A CHROMATOGRAPHY FLOW IN AN LC/NMR ENVIRONMENT

(75) Inventors: Martin Hofmann, Rheinstetten (DE); Manfred Spraul, Ettlingen (DE); Marcus Godejohann, Karlsruhe (DE)

(73) Assignee: Bruker Analytik GmbH, Rheinstetten-Forchheim (DE)

( * ) Notice: Subject to any disclaimer, the term of this patent is extended or adjusted under 35 U.S.C. 154(b) by 35 days.

(21) Appl. No.: 10/014,130

(22) Filed: Oct. 24, 2001

(65) Prior Publication Data

US 2002/0088946 A1 Jul. 11, 2002

(30) Foreign Application Priority Data

Oct. 25, 2000 (EP) ............................ 00123101

(51) Int. Cl.[7] ............................ G01V 3/00; B01D 15/08
(52) U.S. Cl. ............................ 324/321; 422/70; 324/322
(58) Field of Search ............................ 324/321, 318, 324/322, 319, 320; 250/288; 422/70; 356/318; 436/149; 210/635

(56) References Cited

U.S. PATENT DOCUMENTS

| 3,902,848 A | * | 9/1975 | Juvet, Jr. et al. | ............ 436/149 |
| 5,117,109 A | | 5/1992 | Asakawa et al. | ............ 250/288 |
| 5,283,036 A | | 2/1994 | Hofmann et al. | ............ 422/70 |
| 5,449,902 A | | 9/1995 | Onishi et al. | ............ 250/288 |
| 5,898,493 A | * | 4/1999 | Jankowiak et al. | ......... 356/318 |
| 6,497,820 B1 | * | 12/2002 | Goetzinger et al. | ......... 210/635 |

FOREIGN PATENT DOCUMENTS

| EP | 1 001 263 A1 | 5/2000 |
| EP | 1202054 A1 * | 5/2002 |

OTHER PUBLICATIONS

Griffiths, L. and Horton, R., "Optimization of LC–NMR III–Increased Signal–to–Noise Ratio Through Column Trapping," *Magnetic Resonance in Chemistry*, vol. 36, 104–109 (1998), XP002922293.

* cited by examiner

Primary Examiner—Diego Gutierrez
Assistant Examiner—Tiffany A. Fetzner
(74) Attorney, Agent, or Firm—Weingarten, Schurgin, Gagnebin & Lebovici LLP

(57) ABSTRACT

A device for trapping at least one chromatography peak of a chromatography flow comprises at least one trapping column, an inlet capillary for leading the chromatography flow into the trapping column and an outlet capillary departing from the trapping column. A plurality of trapping columns are provided on a column carrier wherein the trapping columns are separately and selectively connectable to and/or removable from the inlet and outlet capillary.

16 Claims, 4 Drawing Sheets

DEVICE FOR TRAPPING AT LEAST ONE COMPONENT OF A CHROMATOGRAPHY FLOW IN AN LC/NMR ENVIRONMENT

BACKGROUND OF THE INVENTION

The invention relates to a device for trapping at least one chromatography peak of a chromatography flow in a system comprising a LC-device and a NMR-detector.

Such a device is known from EP 1 001 263 A1.

A device of the afore-mentioned kind is generally used in liquid chromatography (LC) for trapping and concentrating single chromatography peaks of a chromatography flow, which, for example, have been previously separated in a liquid chromatography separating unit. Trapping and concentrating single chromatography peaks is a known technique for supporting the relatively weak sensitivity of nuclear magnetic resonance (NMR) analysis to which the chromatography peaks are submitted after separation in the LC separating unit for further investigation.

Although the NMR sensitivity is improved constantly, every further improvement is needed. To increase the amount of a separated chromatography peak, several techniques are known. One of them is the so-called solid phase extraction (SPE). In this technique the separated peak is trapped (absorbed) on a chromatographic post column. Using an appropriate treatment of washing and preparing the post column, it will be possible to trap the same chromatographic peak more than once and to concentrate or to accumulate it. Using a back flush option and an optimized desorbing solvent, broad separated trapped peaks will be flushed out as a substantially sharpened peak, in an extent up to a factor of 4. Both effects, the multiple adsorbing and the optimized peak shape are helpful to achieve better results with the NMR.

Lee Griffith and Rob Horton described in their article "Optimization of LC-NMR III-increased signal-to-noise ratio through column trapping" in Chem., Vol. 36, 104–109, 1998, a successful hyphenation of LC-SPE-NMR. They positioned one trapping column between some manual working valves. This construction showed the gain of sensitivity that can be reached with such a system.

In the document EP 1 001 263 A1 mentioned before, a high-performance liquid chromatography apparatus and a process for conversion of mobile phase enabling a trace amount of sample for NMR analysis to be efficiently separated and prepared are disclosed. The method comprises steps of separating target ingredients from the sample by high-performance liquid chromatography, trapping the target ingredient in a trapping column using a different mobile phase, replacing water by deuterium oxide and eluting this target ingredient from the trapping column using deuterated solvent other than deuterium oxide.

All the devices for trapping chromatography peaks known up to now, however, suffer from the disadvantage that they are not flexible in use and are difficult to be integrated in existing LC-NMR systems. Further, automatic software-controlled operation is not possible with these known systems. In any case, manually or offline-driven hardware components are used.

It is, therefore, an object of the present invention to improve a device of the kind mentioned at the outset in that way that the device is more flexible in operation and more flexible in integrating in an existing liquid chromatography system coupled to an analysis detector.

SUMMARY OF THE INVENTION

According to the present invention, this object is achieved with a device for trapping at least one chromatography peak of a chromatography flow in a system comprising a LC-device and a NMR-detector, wherein said trapping device is connected to said LC-device and to said NMR-detector, said trapping device comprising:

a plurality of trapping columns arranged on a column carrier;

an inlet capillary and an outlet capillary, said trapping columns being separately and selectively connectable to said inlet and said outlet capillary;

said column carrier further comprising a first connecting capillary connected to said inlet capillary and a second connecting capillary connected to said outlet capillary, and each of said trapping columns comprising a first capillary connectable to said first connecting capillary and a second capillary connectable to said second connecting capillary in a sealed fashion, said first connecting capillary being detachable from said inlet capillary and said second capillary being detachable from said outlet capillary, wherein said column carrier is removable as a whole with said trapping columns mounted thereon from said trapping device.

The device according to the present invention is more flexible, because a plurality of chromatography peaks of the chromatography flow can be trapped in the plural trapping columns. Full automation of the device according to the present invention is possible, because the single trapping columns can be selectively connected to the inlet and outlet capillary. Further, multiple trapping of the same sample component of the chromatography flow in the same trapping column is also possible after different components have been trapped in other trapping columns. The device according to the present invention renders it possible to run a chromatography in a totally closed system.

The column carrier comprises a first connecting capillary connected to the inlet capillary and a second connecting capillary connected to the outlet capillary, wherein each trapping column comprises a first capillary connectable to the first connecting capillary and a second capillary connectable to the second connecting capillary in a sealed fashion.

The first and second connecting capillary of the column carrier serve as a joint between the trapping column of interest and the remaining part of the device. The trapping column of interest can be exactly positioned relative to the first and second connecting capillary of the column carrier. By virtue of the first and second connecting capillaries, which preferably are immovable, only the trapping columns and their first and second capillaries have to be movable parts of the column carrier.

Further, the first connecting capillary is detachable from the inlet capillary and a second connecting capillary is detachable from the outlet capillary.

This feature has the advantage that the column carrier can be configured as a removable part of the device so that the column carrier can be removed from the device after single peaks of the chromatography flow are trapped in the trapping columns.

Further, the column carrier is removable as a whole with the trapping columns mounted thereon from the device.

This feature has the advantage that a plurality of column carriers can be provided which can be exchanged. This can be useful if the user of the device needs different trapping columns of varying type, e.g. depending on sample polarity, or if the trapping is done in a different location than the subsequent analysis. The column carrier can be stored for several days before the trapped chromatography peaks would be desorbed into the destination detector. In connection with the aforementioned embodiments, the necessary information about the status of each trapping column is stored in a memory and can be read out directly by the device according to the present invention after mounting the column carrier.

In a preferred embodiment, each trapping column, which is not being connected to the inlet capillary and to the outlet capillary, is closed in a sealed fashion.

This feature has the advantage that the influence of the environment is practically not existing. Oxidation processes of the same peaks due to contact with air, decomposition due to light and pollution with dust is excluded.

In a further preferred embodiment, the columns are distributed in a series and the column carrier comprises a drive for moving the selected trapping column in a position for connection with the inlet capillary and the outlet capillary.

This feature has the advantage that the device according to the present invention can be operated without manual interaction, if an appropriate control, in particular a software control, is provided for operating the drive. The drive can be configured as an electrical motor.

In this connection it is preferred, if the column carrier comprises a ring, on an outer periphery of which the trapping columns are disposed, wherein the ring is rotatable.

A construction of the column carrier in form of a ring has the advantage that a great number of trapping columns can be arranged on the column carrier in a space-saving manner. Further, with this configuration the overall dimensions of the column carrier can be held small. However, it is also possible to configure the column carrier as a bar or a slider, if there is no need to save space.

In a further preferred embodiments the first and second connecting capillaries have their open ends mounted on a sealed slider, wherein the ends of the connecting capillaries are directed radially outwardly, and open ends of the first and second capillaries of each trapping column are directed radially inwardly for connection with the open ends of the first and second connecting capillaries.

This feature has the advantage that each trapping column can be exactly connected to the first and second connecting capillaries in a sealed fashion which guarantees the tightness of the connection between the trapping column of interest and the remaining part of the device.

In a further preferred embodiment, the column carrier comprises a control unit for controlling the position of each trapping column with respect to the inlet and outlet capillaries.

This feature enables full automatic operation of the column carrier in order to position the trapping column of interest exactly with respect to the inlet and outlet capillaries.

In a further preferred embodiment, the column carrier comprises a memory for storing data of the current condition of each trapping column.

This feature has the advantage that the actual state of each trapping column can be stored in the memory. This feature is, in particular, useful in case that the column carrier is exchangeable so that information on the state of each trapping column is not lost after removal of the column carrier from the device, because the memory board is integrated in the carrier.

In a further preferred embodiment, the trapping columns have different trapping properties.

By this feature, the flexibility of the device according to the present invention is further enhanced, because different components which need different trapping conditions can be trapped in the appropriate trapping columns, while only one column carrier is needed.

In a further preferred embodiment, the device further comprises at least one first add up flow pump for pumping the chromatography flow by means of at least a first eluent into the selected trapping column, the add up flow pump being connected to the inlet capillary.

This feature improves the trapping conditions and increases the trapping efficiency of the component in the trapping column, whereby the sensitivity gain for the destination detector is increased, too. The add up flow pump pumps the weaker desorbing solvent of the chromatographic separation and is preferably able to add two to four times the volume of the separation applied flow.

In this context it is preferred, if the add up flow pump is connected to the inlet capillary via a switchable valve for connecting and disconnecting the add up flow pump to the inlet capillary.

This feature has the advantage that the add up flow pump can be operated as a permanently working pump, while the pump flow can be interrupted by switching the valve between the open and the closed position.

In a further preferred embodiment, the device further comprises at least a first desorbing pump for pumping at least a second eluent into a selected trapping column for pushing out a peak trapped therein.

The desorbing pump is used to desorb trapped peaks from the trapping columns, for example, to a destination detector, e.g. a NMR detector. The used desorbing eluent is preferably the stronger eluting solvent of the chromatography. The desorbing solvent can be used in deuterated form to avoid large solvent signals and to achieve a better sensitivity, this means that the whole chromatography can be run completely non-deuterated, which has advantages for mass spectroscopy (no molecular ion distribution will be generated for molecules with exchangeable protons) and for the running costs, as normal LC-NMR uses at least one solvent in deuterated form. If the desorbing pump is able to provide more than one solvent, a deuterated weak desorbing solvent can be used to get rid completely of the protonated chromatography solvents. In this case the add up flow solvent mentioned before can be a protonated solvent, because the protonated solvent can be flushed out by the deuterated desorbing solvent provided by the desorbing pump.

In a further preferred embodiment the desorbing pump is connected to the outlet capillary.

This feature has the advantage that the desorbing step can be carried out in the back flush mode, i.e. the desorbing flow is directed in the opposite direction as the flow in the trapping action. By the back flush mode the peak sharpness can be enhanced further, in total up to a factor of 4, using all features mentioned herein.

In a further preferred embodiment, at least one control detector is provided which is disposed in a capillary line selectively connectable to the inlet capillary or the outlet capillary.

This detector can advantageously be used in connection with a peak recognition software for checking in the trapping mode of the device, if the peak to be trapped in the selected trapping column is breaking through. When desorbing a trapped peak from a selected trapping column, a perfect calculation for the timing and positioning of the desorbed peak can be done with this detector.

In a further preferred embodiment, a means for heating and/or cooling the trapping columns is provided.

This feature enables a temperature control of the trapping columns. For preparing each trapping column, it can be useful to heat the trapping columns to a certain temperature in order to be able to try the trapping columns more effectively. With respect to instable peaks trapped in the trapping columns, it can be useful to cool the trapping columns to be sure that the trapped peaks do not precipitate. The means for heating and/or cooling the trapping columns can be provided in the column carrier itself for direct temperature control or in a compartment in which the column carrier is disposed for an indirect temperature control.

In a further preferred embodiment a gas flow source is connectable to the trapping columns.

This feature has the advantage that by means of the gas flow the trapping columns can be dried in a quick and effective manner. In some applications it is helpful to dry the trapping columns after each trapping in order to increase their capacity, in particular in cases of multiple trapping of the same chromatography peak in multiple identical separations in the same trapping columns.

Further, in case that the destination detector is an IR spectrometer, drying will help to get rid of the water which is disturbing a large part of the observable spectrum.

In a further preferred embodiment, each of the trapping columns is connectable to the inlet and outlet capillary again after having been disconnected therefrom for multiple trapping of a same species of chromatography peak in one and the same column.

This feature has the advantage to increase the peak amount on a trapping column which in some applications is urgently needed to achieve the desired detection level, in particular in case of a subsequent NMR detection.

Further features and advantages will be apparent from the following description and the attached drawings.

It will be understood that the above-mentioned features and those to be discussed below, are not only applicable in the given combinations, but may also be employed in other combinations or taken alone without departing from the scope of the present invention.

BRIEF DESCRIPTION OF THE DRAWINGS

Embodiments of the present invention are illustrated in the drawings and will be discussed in more detail below. In the drawings.

DETAILED DESCRIPTION OF A PREFERRED EMBODIMENT

Figure 1:
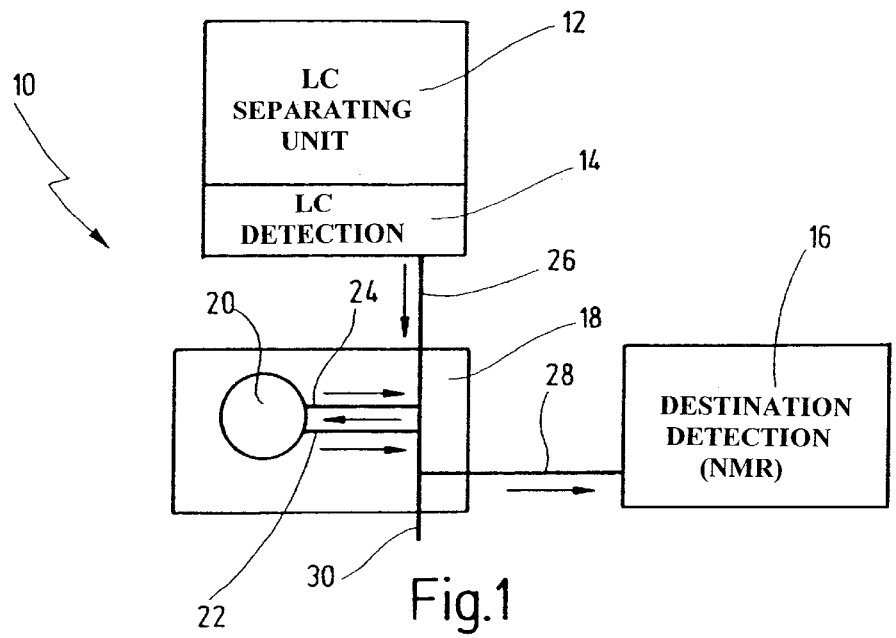
FIG. 1 shows an entire system, comprising a LC separation unit, a device according to the present invention and a destination detector in a schematic representation.

In FIG. 1 an entire liquid chromatography system labeled with reference numeral 10 is depicted in a very simplified block scheme.

The system 10 comprises a liquid chromatography separating unit 12 followed by a chromatography detection unit 14.

The device further comprises a destination detector unit 16, which includes a nuclear magnetic resonance (NMR) detector.

The LC separating unit 12 and the chromatography detection unit 14 are coupled to the destination detector unit 16 via a device 18 for trapping at least one chromatography peak of a chromatography flow coming from the LC separating unit 12 or the chromatography detection unit 14, respectively.

The device 18 not only enables in-line trapping of chromatography peaks, but also allows the other known modes of LC-NMR like on-flow, stopped-flow and time-slicing modes.

The device 18 comprises a column carrier 20 carrying a plurality of trapping columns as will be described in more detail below. The device 18 further comprises an inlet capillary 22 for leading the chromatography flow from the LC separating unit 12 or the chromatography detection unit 14, respectively, to one of the trapping columns carried by the column carrier 20 and an outlet capillary 24 departing from the trapping columns carried by the column carrier 20. "Inlet" and "outlet" are to be understood as flow directions in the trapping mode of the device 18, and can be reverse in the desorbing mode of the device 18.

The device 18 is connected to the LC separating unit 12 or the chromatography detection unit 14 via a capillary 26 leading the chromatography flow into the device 18, and to the destination detector unit 16 via a capillary 28 for leading the chromatography flow from the device 18 to the destination detector unit 16. A capillary 30 is provided for connecting the device 18 to a not shown drain.

As already mentioned before, the device 18 not only allows a trapping of chromatography peaks therein, but also allows a direct connection of the LC separating unit 12 or the chromatography detection unit 14, respectively, with the destination detector unit 16. The arrows in FIG. 1 indicate the possible directions of the chromatography flow in the system 10.

Figure 2:
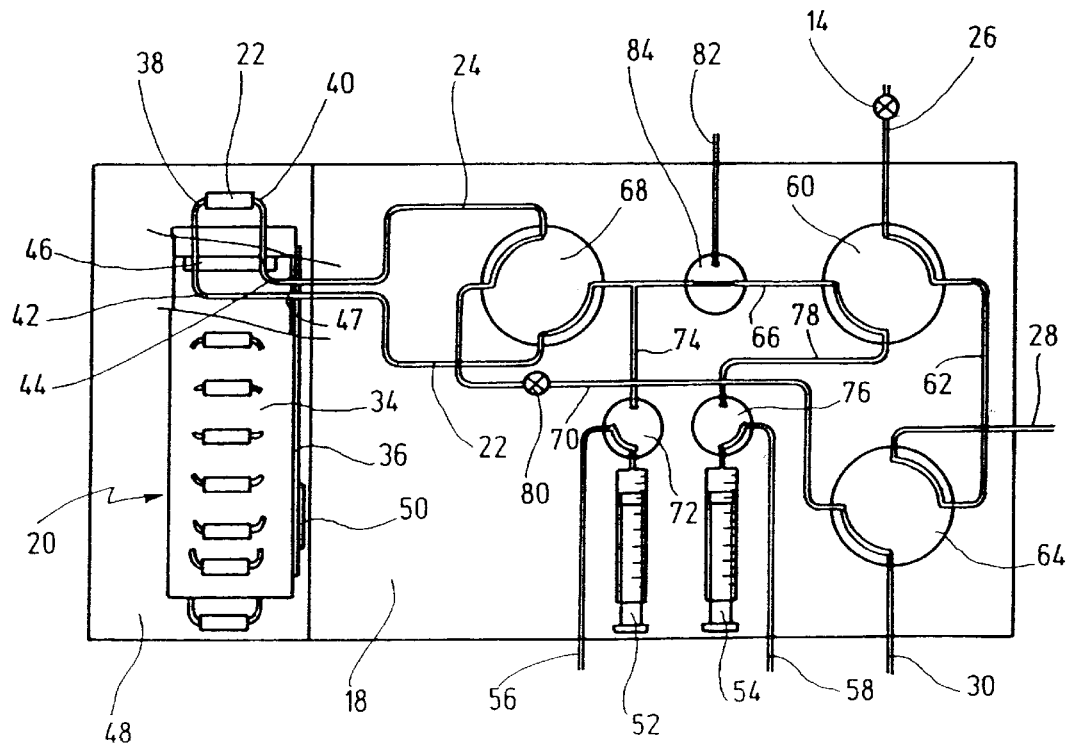
FIG. 2 shows the device according to the present invention in isolation in an enlarged scale in a schematic representation, partially broken, in a first operating position.
Figure 7:
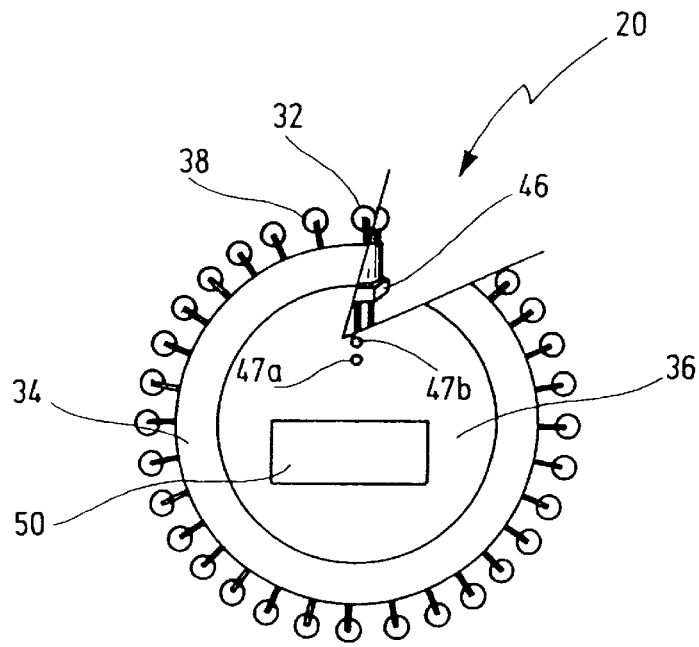
FIG. 7 a column carrier used in the device in FIGS. 2 through 6, partially broken, in a side view.

With reference to FIGS. 2 and 7 the column carrier 20 will be described in more detail.

The column carrier 20 carries a plurality of trapping columns, one of which is labeled with reference numeral 32. In total, the column carrier 20 preferably carries 36 trapping columns 32, but it can carry more or less than 36 columns for compatibility with existing loop collecting systems.

The column carrier 20 comprises an outer ring 34. The trapping columns 32 are disposed on an outer periphery of the ring 34. The ring 34 is rotatably mounted on a body 36 which includes an electronic control (not shown).

Each trapping column 32 comprises a first capillary 38 and a second capillary 40 by which the trapping column 32 is mounted on the outer ring 34 and is secured thereto.

In the body 36 of the column carrier 20 a first connecting capillary 42 and a second connecting capillary 44 are provided for a sealed connection of the first and second capillaries 38 and 40 of the respective selected trapping column 32 with the inlet capillary 22 and the outlet capillary 24. A sealed slider 46 disposed at the outer periphery of the body 36 of the column carrier 20 is provided. The first and second connecting capillaries 42 and 44 have their open ends mounted on the sealed slider 46, wherein the ends of the connecting capillaries 42, 44 are directed radially outwardly, while open ends of the first and second capillaries 38 and 40 of each trapping column 32 are directed radially inwardly for a sealed connection with the open ends of the first and second connecting capillaries 42 and 44.

A drive (not shown) is provided for rotating the outer ring 34 relative to the body 36 and, thus, the trapping columns 32 can be moved with their first and second capillaries 38 and 40 relative to the sealed slider 46 for connection of the respective first and second capillaries 38 and 40 of the respective trapping column 32 with the first and second connecting capillaries 42 and 44, and, via these with the inlet and outlet capillaries 22 and 24.

Instead of having first and second capillaries 38 and 40, each trapping column 32 can be mounted directly into the outer ring 34. All connections between the capillaries mentioned before are totally sealed.

As already mentioned before, the control unit disposed in the body 36 of the column carrier 20 is able to check every position of each trapping column 32 to enable the exact position of the first and second capillaries 38 and 40 of the trapping columns 32 with respect to the sealed slider 46. The drive for rotating the outer ring 34 preferably is an electrical motor.

Further, the first and second connecting capillaries 42 and 44 are detachably connected to the inlet and outlet capillaries 22 and 24. Again, the connection between the first and second connecting capillaries 42 and 44 and the inlet and outlet capillaries 22 and 24 are totally sealed.

The column carrier 20 is arranged in a compartment 48 of the device 18, from which the column carrier 20 is removable. An engine-driven slider moving the column carrier 20 in the compartment 48 and out of the compartment 48 can be used. With the column carrier 20 being a removable part of the device 18, several column carriers 20 having trapping columns 32 with different trapping properties can be used. Also, the trapping columns 32 of the same column carrier 20 can be chosen with different trapping properties.

Further, the column carrier 20 comprises a memory 50 for storing data of the current condition and status of each trapping column 32. The status of each trapping column 32 which can be stored in the memory 50 is, for example, "free and prepared", "free and not prepared", "occupied with a peak (including peak data)", and so on. The memory 50 allows removal of the column carrier 20 from the compartment 48 without losing information on the status of each trapping column 32.

The column carrier 20 can be stored for several days before the peaks trapped therein will be desorbed into the destination detection unit 16. The necessary information about the status of each trapping column 32 is stored in the memory 50 and can be read out directly by the device 18 after mounting the column carrier 20 in the compartment 48. In case that the column carrier 20 comprises different trapping columns 32 with different trapping properties, the information stored in the memory 50 can also distinguish the column type. A software can be provided which is able to chose, depending on the separation conditions, the right trapping column 32 for optimized operation.

Further, a means (not shown) for heating and/or cooling the trapping columns 32 is provided. Such means can be provided by a temperature control of the compartment 48 itself, thus indirectly controlling the temperature of the trapping columns 32.

Further, it is to be noted that each trapping column 32 which is not actually connected with the inlet and outlet capillaries 22 and 24 is closed in a sealed fashion so that a peak trapped therein is not in contact with the environment.

With respect to FIG. 2, the device 18 comprises at least one add up flow pump 52 and at least one desorbing pump 54.

The add up flow pump 52 is connected to a solvent reservoir (not shown) via a capillary 56. The desorbing pump 54 is connected to a further solvent reservoir (not shown) via a capillary 58.

The add up flow pump 52 pumps the weaker desorbing solvent of the chromatographic separation. The add up flow pump 52 is able to add two to four times the volume of the separation applied flow. The desorbing pump 54 pumps a solvent which is the stronger eluting solvent of the chromatography. This solvent can be used in deuterated form to avoid large solvent signals and to achieve a better sensitivity.

The solvent pumped by the add up flow pump 52 can be a protonated solvent in case that the desorbing pump 54 can provide more than one solvent.

The add up flow pump 52 and the desorbing pump 54 are shown in the figures as syringe pumps, which is just a symbol for any suited pump. Further, more than one add up flow pump and more than one desorbing pump can be provided if appropriate. The pumps 52 and 54 can be permanently working pumps.

In the following, the remaining components of the device 18 are described.

The capillary 26 coming from the LC separating unit 12 or the chromatography detection unit 14, respectively, are connected to a valve 60. The valve 60 is a 4-port valve.

Figure 4:
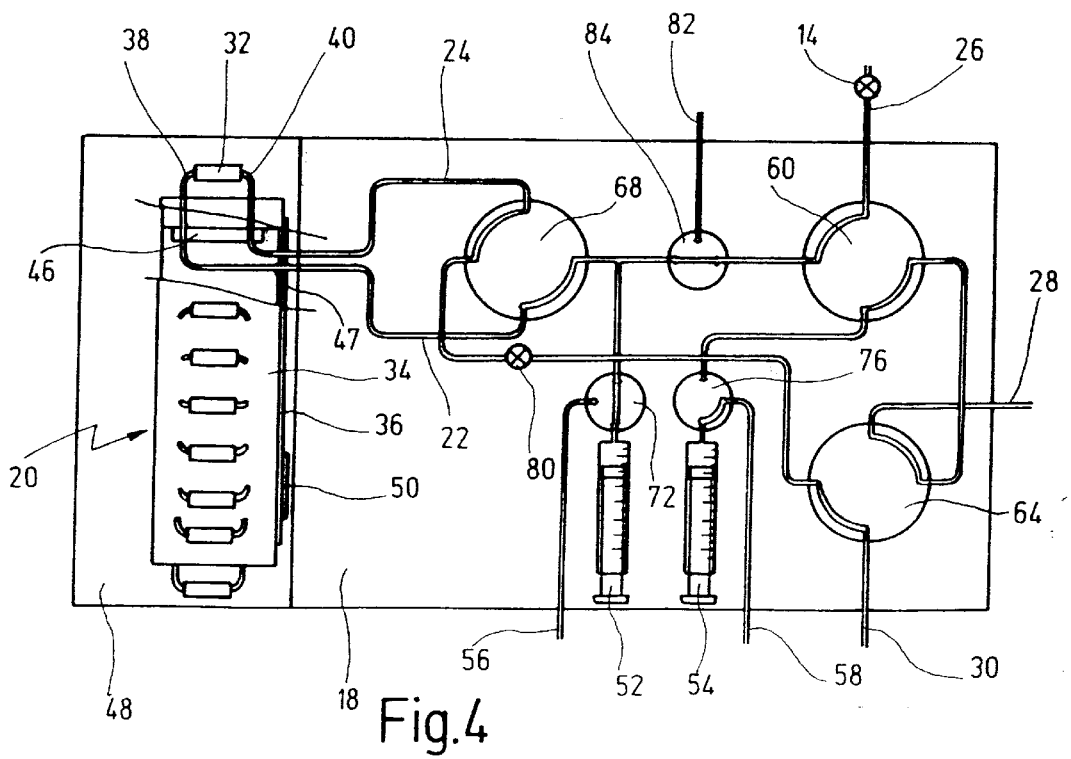
FIG. 4 the device in FIGS. 2 and 3 in a third operating position during the trapping action.

By means of the valve 60, the capillary 26 can be either connected to the capillary 28 via a capillary 62 and a second valve 64, which is also a 4-port valve as shown in FIG. 2, or can either be connected to a capillary 66 and a third valve 68, which also is a 4-port valve, as shown in FIG. 4.

The outlet capillary 24 and the inlet capillary 22 in turn are connected to the third valve 68. The capillary 66 is disposed between the first valve 60 and the third valve 68. A further capillary 70 is connected to the third valve 68 and to the second valve 64.

The add up pump flow 52 is connected to the capillary 66 via a fourth valve 72, which is a 3-port valve, and via a capillary 74 which is connected to the capillary 66 via a T-piece.

The desorbing pump 54 is connected to the first valve 60 via a fifth valve 76, which is a 3-port valve, and via a capillary 78.

A control detector 80, which can be of the same type as the chromatography detection unit 14, for example a UV detector, is disposed in the capillary 70.

Finally, a not shown gas flow source is connected to the capillary 66 via a capillary 82 and a fifth valve 84, which is a 3-port valve.

All the valves and capillaries mentioned before are designed with a low dead volume to avoid chromatography peak broadening. All the components mentioned before should be placed as close as possible. The capillaries used in the system to connect the single parts to each other should have small inner bores for the same reason of avoiding chromatography peak broadening. A maximum inner diameter of 0.25 mm is preferred. The material of the valves mentioned before should be inert to the standard chromatographic solvents. As the trapping columns 32 can create a substantial back pressure, not only the valves, but also the other parts of the device 18 and connectors should stand the occurring pressures.

In the following, the work flow of the device 18 will be described.

Figure 3:
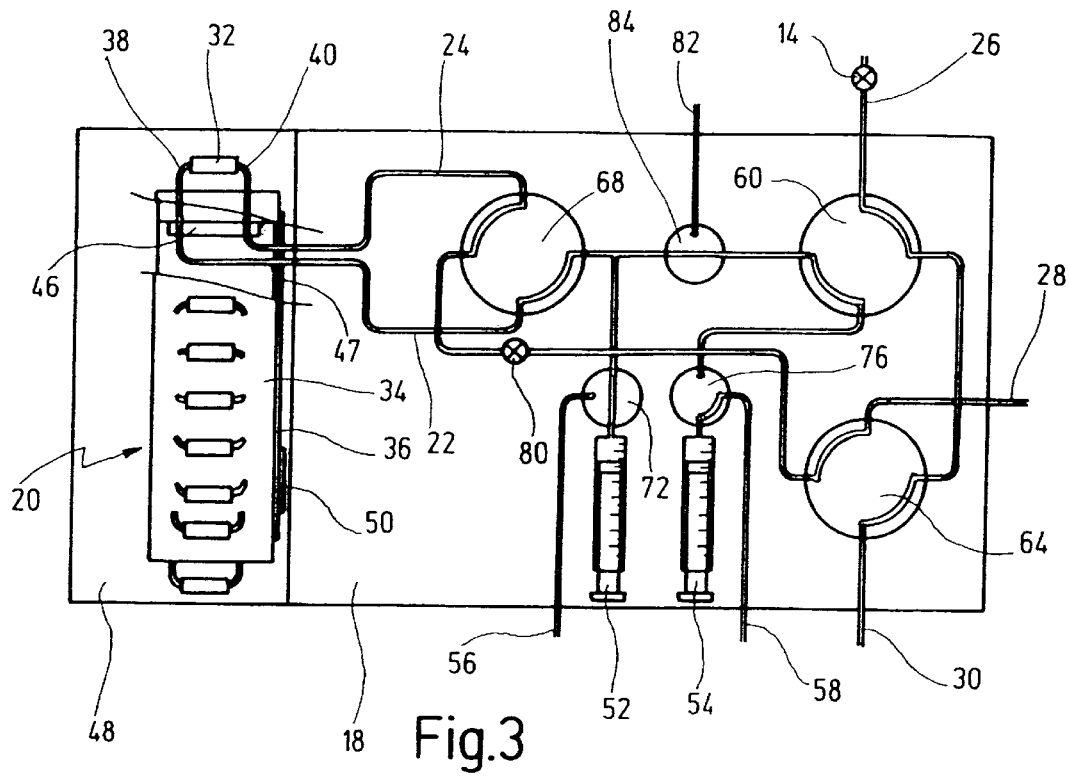
FIG. 3 the device in FIG. 2 in a second operation position prior to the trapping action.

In FIG. 2 the device 18 is shown in an operating position where the valve 60 and the valve 64 are switched such that the chromatography flow coming through the capillary 26 is led via the capillary 62 into the capillary 28 leading to the destination detector unit 16. This position of the valves 60 and 64 allows the on-flow and stopped-flow modes, as is known from the traditional systems, for example traditional LC-NMR systems. The signal coming from the chromatography detection unit 14 can be used to trigger the stop of the chromatography in the stopped-flow mode. Based on the signal from the chromatography detection unit 14, a suited automated peak detection software makes the decision, if the peak will be of interest or not. In case of a chromatography stop, the valve 64 switches into the drain position as shown in FIG. 3 connecting the capillary 62 with the capillary 30. By switching the valve 72 of the add up flow pump 52 as shown in FIG. 3, the preparation of a selected trapping column 32 can be performed. Flushing the trapping column 32 with the weaker absorbing solvent helps to increase the retention on the column material and is essential for the trapping success.

FIG. 3 shows the initial position of the trapping mode of the device 18. The valve 64 is in the operating position connecting the capillary 26 with the capillary 30 to drain. The add up flow pump 52 is pumping permanently the weaker absorbing solvent to keep the trapping column 32 under optimized conditions. If an interesting peak is detected by the chromatography detection unit 14, the valve 16 switches into the operating position shown in FIG. 4 connecting the capillary 26 with the capillary 66, while the valve 68 is in an operating position connecting the capillary 66 with the inlet capillary 22.

In FIG. 4 the operating position of the valves 60 and 68 for the trapping action is shown. The interesting part of the detected peak will be led through the trapping column 32. Due to the dilution of the chromatography flow by the add up flow pump 52, the retention behavior on the trapping column 32 can be improved. The detector 80, which is in the operating position of the valve 68 as shown in FIG. 4 connected via the capillary 70 with the outlet capillary 24 can be used to check if the trapped peak is not breaking through, but trapped completely. The trapping time is calculated dependent on the flow rate. After the peak of interest is successfully trapped on the trapping column 32, the valves 68 and 60 are switched back to the position in FIG. 3. The next free trapping column 32 will be driven to the sealed slider 46.

It goes without saying that not only one, but also multiple injections can be carried out as long as there are free trapping columns 32.

If the same sample component of the chromatography flow is coming later on again, a mode will be provided to trap the same peaks on the same trapping column 32. This mode will help to increase the peak amount on a trapping column 32 which in a lot of applications is urgently needed to achieve the desired detection level in case of a subsequent NMR detection.

Figure 5:
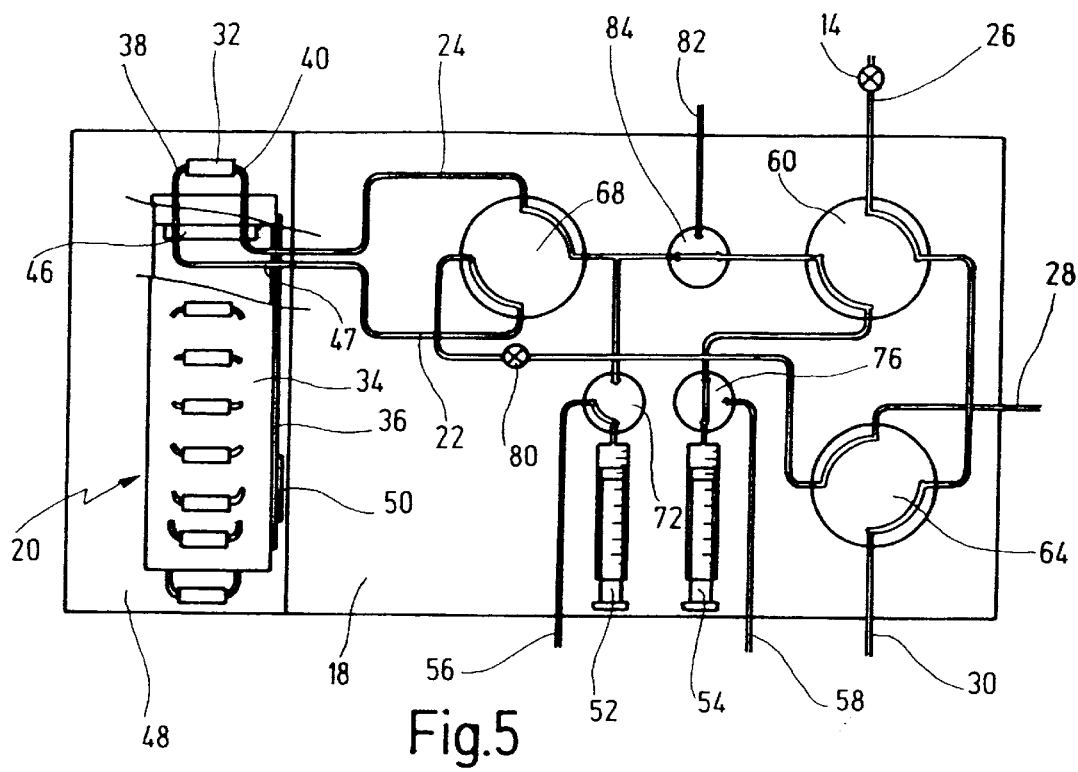
FIG. 5 the device in FIGS. 2 through 4 in a fourth operating position during the desorbing action.

FIG. 5 shows the desorbing action of the device 18. The desorbing action can be carried out any time after the chromatography separation and trapping has finished. Even several days between trapping and desorbing will not impact the quality, if the storage of the column carrier 20 is done in a proper way. The means for heating and/or cooling the trapping columns can be used for cooling the trapping columns 32 for this purpose.

The desorbing pump 54 is now switched into the flow path, i.e. the desorbing pump 54 is connected via the valve 76, capillary 78, valve 60, capillary 66, valve 68 with the outlet capillary 24. In other words, the valve 68 is switched in an operating position to reverse the flow in a so-called back flush mode. The back flushing mode will have an additional positive effect to the peak shape in the sense that the peak shape is sharpened. The release of the trapped peak in the selected trapping column 32 is done in pumping a strong desorbing solvent through the trapping column 32 to the destination detector unit 16. Preferably a fully deuterated solvent will be provided. The detector 80, which is in the operating position of valve 68 connected to the inlet capillary 22, which in turn is in the desorbing action the outlet capillary for the peak flow, can be used for an exact calculation for the timing and positioning of the desorbed peak. The transfer time and transfer volume to the destination detector unit 16 can be based on the peak maximum signal of the detector 80.

Figure 6:
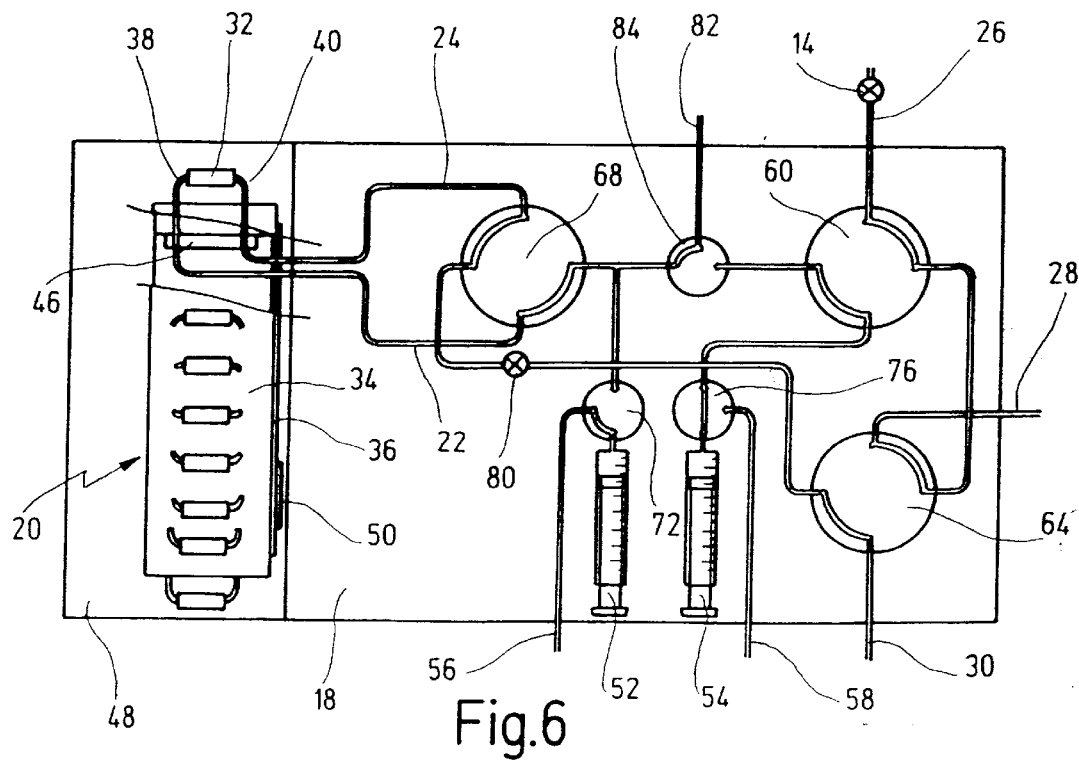
FIG. 6 the device in FIGS. 2 through 5 in a fifth operating position during a drying action.

In FIG. 6 the valve 84 is switched into an operating position in which the gas flow source (not shown) is connected via the capillary 82, the capillary 66, the valve 68 with the inlet capillary 22. In this operating position, the trapping column 32 can be dried. This action is preferably done if multiple injections with multiple trapping are performed in the same trapping columns 32. Drying will ensure that the peak fraction trapped before is not flushed out of the trapping column 32 by the next peak fraction, which will be trapped on the same trapping column 32.

Figure 8:
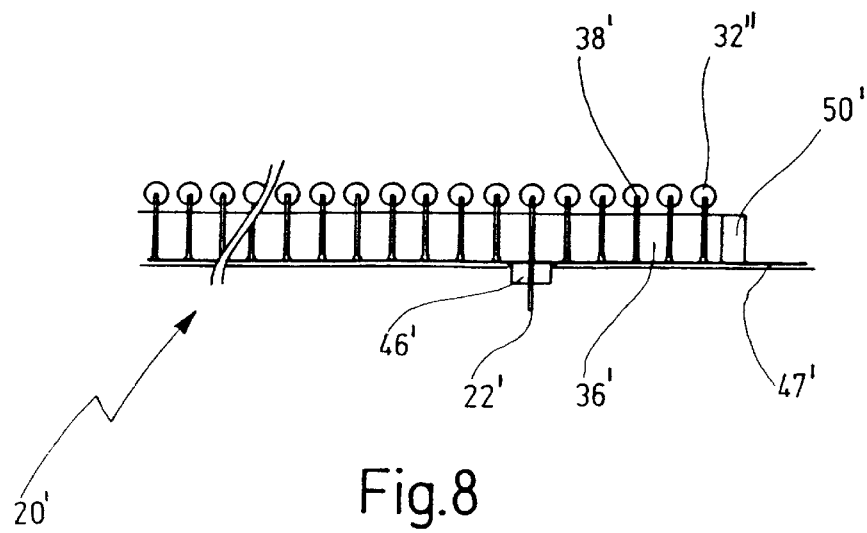
FIG. 8 a column carrier according to a second embodiment for use in the device in FIGS. 2 through 6.

Finally, in FIG. 8 another embodiment of a column carrier 20' is shown. The column carrier 20' is formed as a bar, which can be considered as an open ring. Parts of the column carrier 20' corresponding to the same parts of the column carrier 20 are labeled with the same reference numerals supplemented by a dash. Instead of a configuration of the column carrier 20 in form of a ring or a bar, it is also thinkable to form the column carrier 20 as an array.

What is claimed is:

1. A device for trapping at least one chromatography peak of a chromatography flow in a system with a LC-device and a NMR-detector, wherein said trapping device is connected to said LC-device and to said NMR-detector, said trapping device comprising:

a plurality of trapping columns arranged on a column carrier;

an inlet capillary and an outlet capillary, said trapping columns being separately and selectively connectable to said inlet and said outlet capillary;

said column carrier having at least a first connecting capillary connected to said inlet capillary and a second connecting capillary connected to said outlet capillary, and each of said trapping columns having at least a first capillary connectable to said first connecting capillary and a second capillary connectable to said second connecting capillary in a sealed fashion, and first connecting capillary being detachable from said inlet capillary and said second capillary being detachable from said outlet capillary, wherein said column carrier is removable as a whole with said trapping columns mounted thereon from said trapping device.

2. The device of claim 1, wherein each of said trapping columns which is not being connected to said inlet capillary and to said outlet capillary is closed in a sealed fashion.

3. The device of claim 1, wherein said trapping columns are distributed in a series and said column carrier comprises a drive for moving a selected one of said trapping columns in a position for connection with said inlet capillary and said outlet capillary.

4. The device of claim 3, wherein said column carrier comprises a ring, on an outer periphery of which said trapping columns are disposed, wherein said ring is rotatable.

5. The device of claim 4, wherein said first and second connecting capillaries have their open ends mounted on a sealed slider, wherein ends of said first and second connecting capillaries are directed radially outwardly, and open ends of said first and second capillaries of each of said trapping columns are directed radially inwardly for connection with said open ends of said first and second connecting capillaries.

6. The device of claim 1, wherein said column carrier comprises a control unit for controlling the position of each of said trapping columns with respect to said inlet and outlet capillaries.

7. The device of claim 1, wherein said column carrier comprises a memory for storing data of a current condition of each trapping column.

8. The device of claim 1, wherein said trapping columns have different trapping properties.

9. The device of claim 1, wherein said device further comprises at least one first add up flow pump for pumping said chromatography flow by means of at least a first eluent into a selected one of said trapping columns, said add up flow pump being connected to said inlet capillary.

10. The device of claim 9, wherein said add up flow pump is connected to said inlet capillary via a switchable valve for connecting and disconnecting said add up flow pump to said inlet capillary.

11. The device of claim 1, wherein said device further comprises at least a first desorbing pump for pumping at least a second eluent into a selected trapping column for pushing out a peak trapped therein.

12. The device of claim 11, wherein said desorbing pump is connected to said outlet capillary.

13. The device of claim 1, wherein at least one control detector is provided which is disposed in a capillary line selectively connectable to said inlet capillary or said outlet capillary.

14. The device of claim 1, wherein a means for heating and/or cooling said trapping columns is provided.

15. The device of claim 1, wherein a gas flow source is connectable to said trapping columns.

16. The device of claim 1, wherein each of said trapping columns is connectable to said inlet and outlet capillary again after having been disconnected therefrom for multiple trapping of a same species of chromatography peak in one and the same trapping column.

* * * * *

UNITED STATES PATENT AND TRADEMARK OFFICE
CERTIFICATE OF CORRECTION

| | |
|---|---|
| PATENT NO. | : 6,614,228 B2 |
| DATED | : September 2, 2003 |
| INVENTOR(S) | : Martin Hofmann et al. |

It is certified that error appears in the above-identified patent and that said Letters Patent is hereby corrected as shown below:

<u>Column 3,</u>
Line 37, "embodiments the" should read -- embodiment, the --.

Signed and Sealed this

Fourteenth Day of September, 2004

JON W. DUDAS
*Director of the United States Patent and Trademark Office*